United States Patent [19]
Berryman et al.

[11] Patent Number: 5,830,230
[45] Date of Patent: Nov. 3, 1998

[54] METHOD OF INTRACRANIAL VASCULAR EMBOLOTHERAPY USING SELF ANCHORING COILS

[75] Inventors: Thomas J. Berryman; Jay Lenker, both of San Clemente, Calif.

[73] Assignee: Micro Therapeutics, Inc., San Clemente, Calif.

[21] Appl. No.: 813,613

[22] Filed: Mar. 7, 1997

[51] Int. Cl.⁶ .................................................. A61M 29/00
[52] U.S. Cl. .......................................... 606/200; 606/198
[58] Field of Search ................................ 604/52, 53, 48, 604/49, 104, 106, 93, 280, 281; 606/191, 194, 195, 198, 200

[56] References Cited

U.S. PATENT DOCUMENTS

| | | | |
|---|---|---|---|
| 4,619,246 | 10/1986 | Molgaard-Nielsen et al. | 128/1 R |
| 4,994,069 | 2/1991 | Ritchart et al. | 606/191 |
| 5,256,146 | 10/1993 | Ensminger et al. | 604/104 |
| 5,383,887 | 1/1995 | Nadal | 606/200 |
| 5,527,338 | 6/1996 | Purdy | 606/200 |
| 5,540,680 | 7/1996 | Guglielmi et al. | 606/32 |
| 5,562,698 | 10/1996 | Parker | 606/200 |
| 5,582,619 | 12/1996 | Ken | 606/191 |
| 5,634,942 | 6/1997 | Chevillon et al. | 623/1 |
| 5,690,667 | 11/1997 | Gia | 606/191 |

*Primary Examiner*—Wynn Wood Coggins
*Assistant Examiner*—Cris L. Rodriguez
*Attorney, Agent, or Firm*—Crockett & Fish; K. David Crockett, Esq.

[57] ABSTRACT

A method of intracranial placement of an embolization coil provided with an anchor to prevent migration of the coil after placement.

2 Claims, 4 Drawing Sheets

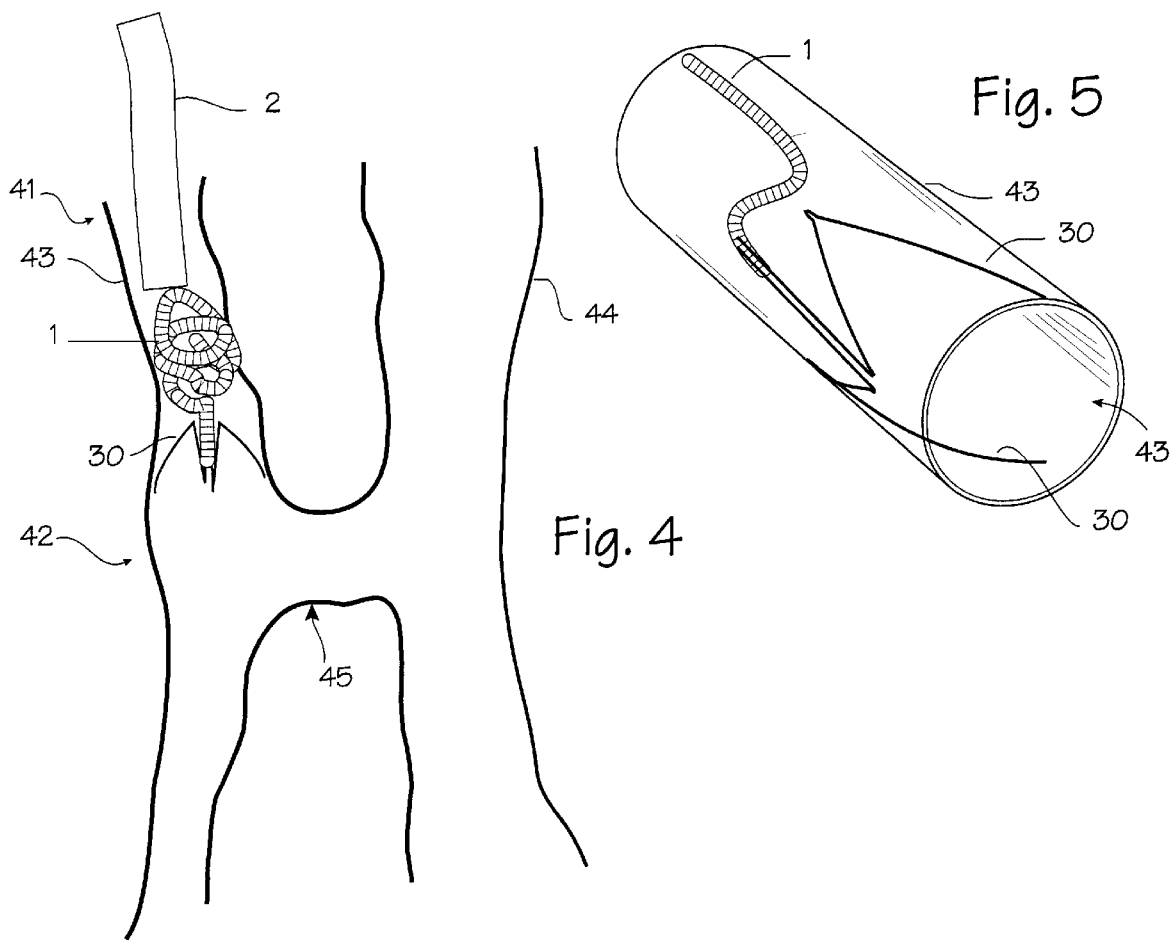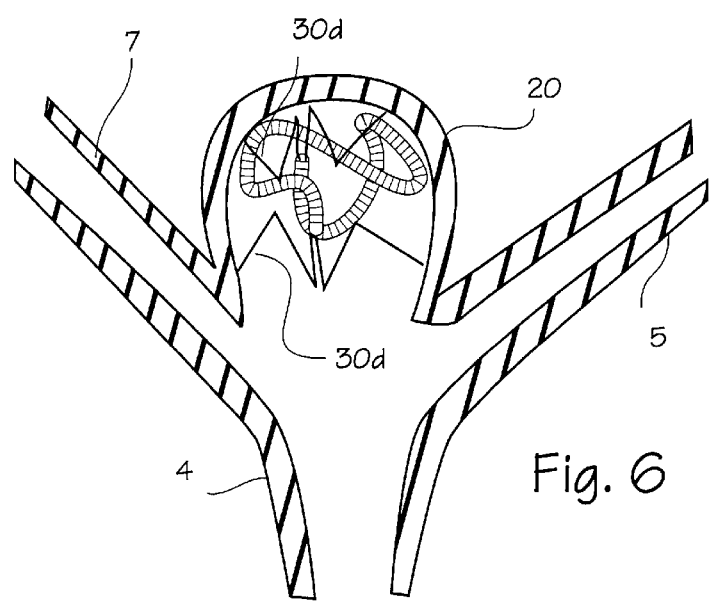

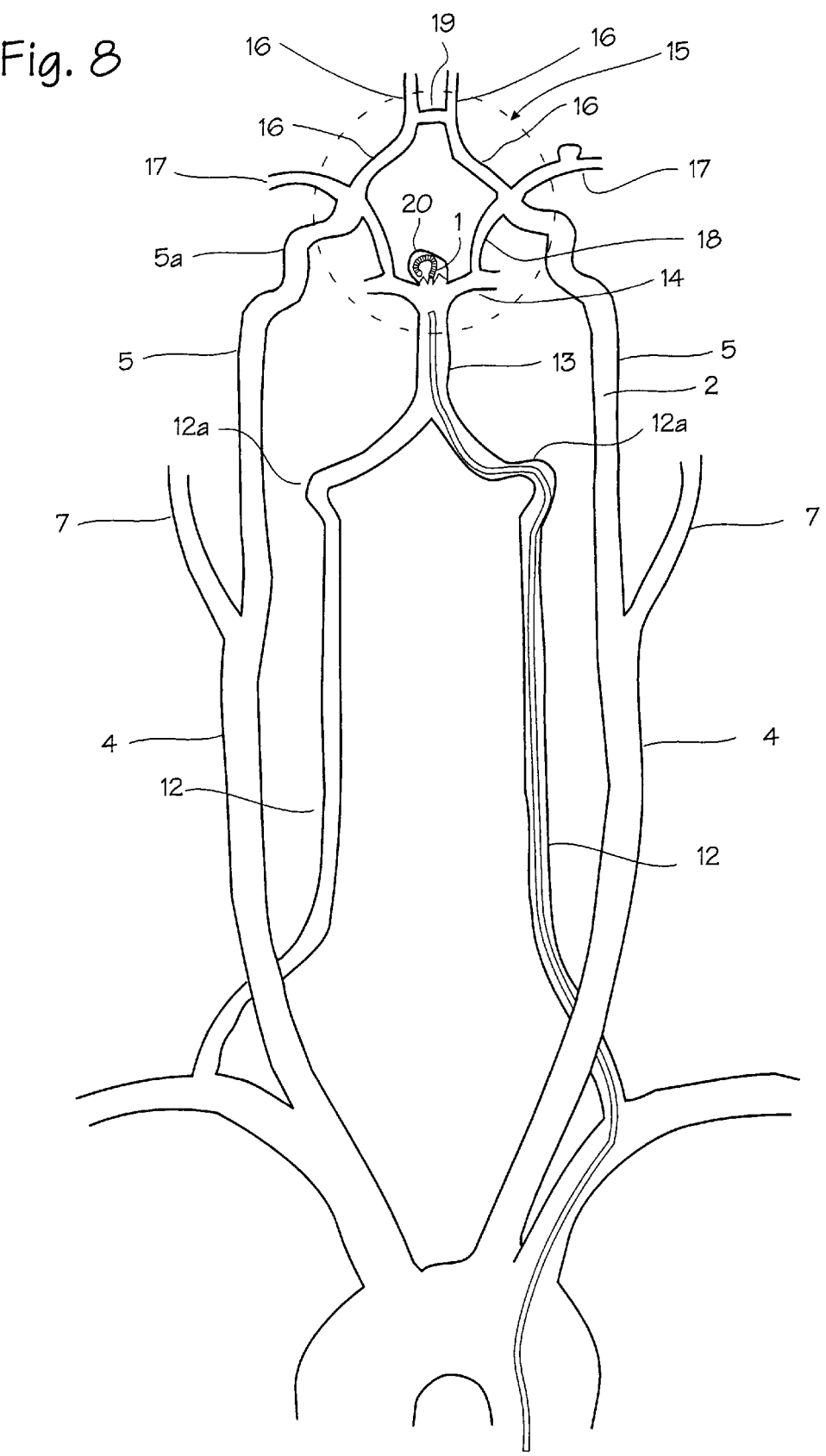

METHOD OF INTRACRANIAL VASCULAR EMBOLOTHERAPY USING SELF ANCHORING COILS

FIELD OF THE INVENTION

This invention relates to methods of using occlusive devices for use in vascular surgery of the brain.

BACKGROUND OF THE INVENTION

Numerous diseases and conditions of the circulatory system and other organs of the body are beneficially treated by the occlusion of blood vessels. Arteriovenous fistulas, arteriovenous malformations, aneurysms and pseudoaneurysms, patent ductus arteriosus, gastrointestinal bleeding, renal and pelvic bleeding, and tumors are examples of the numerous maladies that can be treated by blocking associated blood vessels. Placement of various substances within the blood vessels is one of the methods of encouraging the formation of thrombus (clot) which leads to the complete occlusion of the blood vessels. As early as 1975, coils were successfully used to occlude the renal arteries. Gianturco, et al., Mechanical Devices for Arterial Occlusions, 124 Am. J. Roent. 428 (1975). The purpose of the coil is to encourage quick formation of a thrombus (a blood clot) around the coil. The coils are currently in use for a wide range of treatments, and are referred to variously as occlusive coils, embolization coils, or Gianturco coils. They are commercially available from Cook, Inc. and Target Therapeutics, Inc.

Of the many diseases that may be treated with embolic coils, aneurysms are of particular interest. Embolization coils of appropriate size for placement within aneurysms are commercially available from Target Therapeutics, Inc. Embolization coils made with electrolytic mechanisms for detachment from the delivery catheter are referred to as GDC's or Guglielmi Detachable Coils. the use of GDC's is illustrated, for example, in Klein, et al., Extracranial Aneurysms and Arteriovenous Fistula: Embolization with the Guglielmi Detachable Coil, 201 Radiology 489 (1996). Use of the GDC coils within the brain is illustrated, for example, in Casasco, et al., Selective Endovascular Treatment Of 71 Intracranial Aneurysms With Platinum Coils, 79 J. Neurosurgery 3 (1993).

Because Gianturco and Guglielmi coils are often used to occlude aneurysms in critical areas of the body, it is important that they remain in place where they are implanted. However, migration of the coils after placement is a common but dangerous problem encountered with these coils. Watanabe, Retrieval Of A Migrated Detachable Coil, 35 Neuro. Med. Clin. 247 (1995) reports the migration of a coil from a placement in the superior cerebellar artery into the basilar artery. Halbach, et al., Transarterial Platinum Coil Embolization Of Carotid Cavernous Fistulas, 12 AJNR 429 (1991) reports the migration of a coil from the internal carotid artery. Migration is particularly common with coils placed in wide neck aneurysms. The possible migration of coils is a danger that must be considered in every procedure, and actual migration can be a life threatening complication, since embolization at an unwanted site could occlude a critical blood flow. Migration of the coil may also represent a failure of the intended therapeutic procedure.

SUMMARY

The method of treating intra-cranial vascular disease comprises placement of anchored embolization coils within the intra-cranial vasculature as a means of occluding select portions of the intracranial vasculature. The devices used in the method comprise an anchoring system attached to a modified stainless steel Gianturco occluding coil. The combination creates a mechanical occluding device that can produce a limited size vascular occlusion and can also be used in non-tapering vascular structures in which the possibility of migration is very high. In the brain, such structures may include arterio-venous fistulas, aneurysms and pseudoaneurysms. The anchor is meant to keep the coil in place and prevent migration. The anchoring system is made of spring wires, bars or leafs that extend from the distal or proximal end (or both) of the embolization coil, and expand against the blood vessel in which they are placed, thereby providing additional stability to the embolization coils and preventing migration of the coils.

BRIEF DESCRIPTION OF THE DRAWINGS

FIG. 4 is a view of the anchored embolization coil deployed within a blood vessel near a site of disease.

FIG. 5 is a perspective view of the anchor and embolization coil deployed within a blood vessel.

FIG. 6 is view of the anchored embolization coil deployed within an aneurysm.

FIG. 8 is schematic diagram of the vasculature of the brain illustrating the circle of Willis and arteries supplying the circle of Willis.

DETAILED DESCRIPTIO OF THE INVENTION

Figure 1:
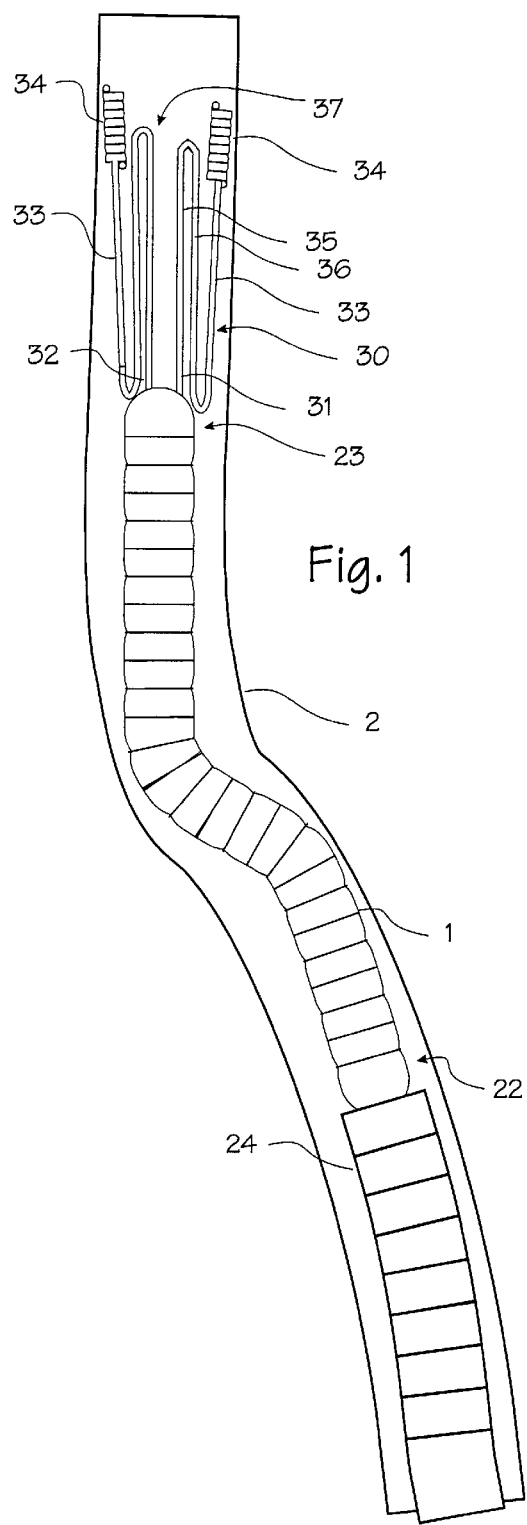
FIG. 1 is a view of the anchored embolization coil housed within a delivery catheter.

FIG. 1 shows a close-up view of the occlusive coil 1 disposed within a delivery catheter 2. The coil may be any of several coils previously proposed and used to stuff blood vessels, fistulas and aneurysms, such as the GDC coils marketed by Target Therapeutics, Inc. or the Gianturco coils marketed by Cook, Inc. Each coil 1 has a proximal end 22 and a distal end 23. The coils may be pushed out of the delivery catheter using the pushing wire 24, which may be any suitable guide wire or small catheter inserted within the delivery catheter. Pushing and detachment of the coils can be accomplished by a variety of other methods, such as the pushrod, pullback of the delivery catheter or other methods. The connection between the delivery catheter/push rod assembly may be a quick release type or an easily severable connection, or may be a mere containment within the catheter. Severable retaining cords, electrolytically severable joints, or miniature quick release or latching mechanisms may be used. The coil is sized and dimensioned to fit into the target site, which may be an aneurysm such as the aneurysms illustrated in FIGS. 7 and 8. For intracranial use, the coil will be in the range of about 2 mm diameter and 10 cm long. The coils are typically made of stainless steel, and may be made of other materials such as nitinol, tantalum, platinum, etc. The coils may be coated with a thrombogenic coating or may be made with a thrombogenic substance such as an electro-positive substance. Platinum is an electropositive substance that may be used either as the coil material or as a coil coating. The coils may fit within standard and commercially available delivery catheters, and may be stretched into a straight line configuration to fit within the lumen of small diameter delivery catheters. Depending on the materials, the coils may be spring biased or provided with shape memory to assume the shape of a helical coil, rosette shape, pretzel shape or other shape, or an irregular tangle when unrestrained.

Figure 2:
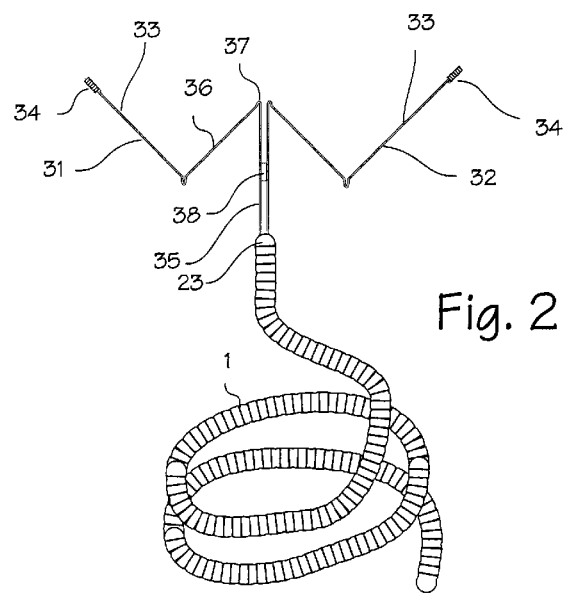
FIG. 2 is a view of the anchored embolization coil in its relaxed state.

FIG. 1 shows the embolization coil 1 fitted with an anchor 30. The anchor is affixed distal end 23 of the coil 1, but may also be affixed to the proximal end, or to both ends. The anchor is comprised of two stainless steel wires 31 and 32 which are bent twice to form an anchor having a W-Shape. The free legs 33 of the anchor are blunted and reinforced using pieces of a small diameter coil 34 to prevent perforation of the vessel wall. While the anchor may be of many configurations, the anchor illustrated in FIG. 1 is further characterized by a shank 35, arms 36 which extend rearwardly from the crown 37, and flukes comprised of the small diameter coils 34. The arms 36 are bent to create a leaf spring arrangement, and the wires comprising the anchor are spring biased to expand in the open W or M position mounted on the shank 35 as shown in FIG. 2. As an alternative to spring biased stainless steel or other spring metal, superelastic or shape memory alloys and compositions may be used.

Figure 3:
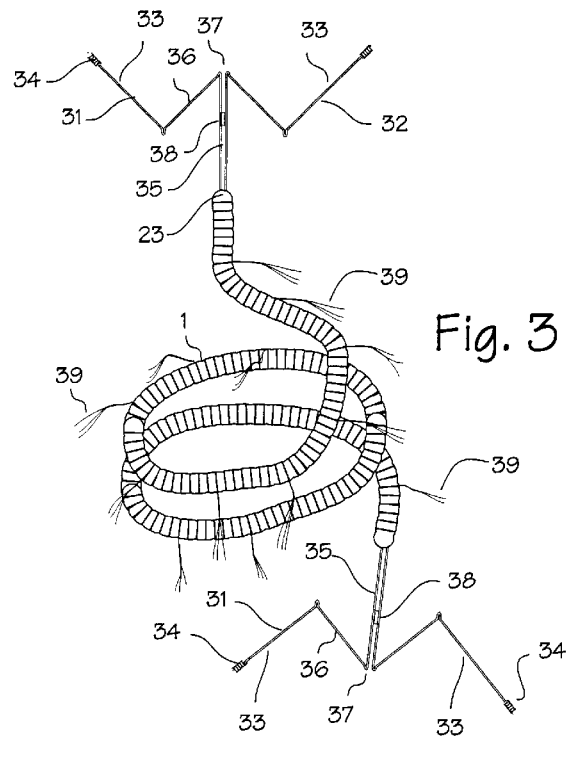
FIG. 3 is a view of the double anchored embolization coil in its relaxed state.

As shown in FIG. 2, the embolization coil 1 when unrestrained reverts to its own biased shape (here a coil), and the attached anchor 30 when unrestrained opens into the W configuration mounted upon the shank 35. The spring biased arms have opened away from the axis of the coil 1, and will open until they impinge upon the wall of the blood vessel in which they are deployed. The wire section forming the shank 35 is reinforced with small support 38 which helps keep the shank oriented in proper relation to the coil. FIG. 3 illustrates that the coil may be provided with an additional anchor 30p at the proximal end of the coil, thus forming an embolization coil having anchors at both ends of the coil. Another feature illustrated in FIG. 3 is the thread attachments 39 (also called strands or tails) which are fastened to the coil 1 at various positions along the length of the coil. These threaded attachments further promote the formation of thrombus around the coil. The threaded attachments may be added to any embodiment of the anchored embolization coil, and may be made of Dacron, polyester, silk or wool or other suitable material.

FIG. 4 shows the embolization coil 1 with an anchor deployed within a blood vessel 41 with a diseased site 42. The diseased site may be an aneurysm, fistula or other disease distal to the site of deployment, but in the case of FIG. 4 a fistula is chosen to illustrate the operation of the coil. The anatomy shown in FIG. 4 is an artery 43 and a vein 44 which are connected via the fistula or arterio-venous shunt 45. The artery and vein should not be directly connected, but should be indirectly connected through a capillary bed. The fistula 45 can be the result of injury, poor healing after surgery, or congenital defect. In any case, the abnormal connection through the fistula 45 should be occluded. To accomplish this, the anchored embolization coil 1 is placed via the delivery catheter 2 into the artery 43 just upstream in the blood flow from the fistula 45. After release from the delivery catheter the coil is transformed by virtue of its spring bias into the helical shape, and fills a substantial portion of the blood vessel 41. The anchor 30 has also opened toward its unrestrained shape to the extent allowed by the blood vessel wall. The arms of the anchor are urged by spring force into contact with the blood vessel wall. The slight force applied by the spring bias of the anchor 30 on the wall anchors the embolization coil 1 into place. The anchor may bend to conform to the internal diameter of the blood vessel. The free legs 33 and the arms 36 define a semicircular arc across the lumen of the blood vessel. In addition to the placement of coil 1, the space upstream of the coil and anchor can also be filled with additional released coil turns. Thus, the coil conglomerate can be made more compact improving the stabilization of the device further.

When deployed within a generally cylindrical vessel such as the artery 43, the anchor will bend to conform to the inner surface of the artery, as illustrated in FIG. 5. FIG. 5 shows a perspective view of the artery and anchor within the artery. The anchor 30 has arched into conformance with the inner surface of the artery, in this case taking on the shape of an M or W mapped onto the inside of the generally cylindrical shape of the blood vessel. Because the anchor arches around the wall of the blood vessel, the central portion of the lumen which is co-extensive with the anchor is left unfilled, making it possible to either apply additional occluding material in the proximal space 46 in front of the embolization coil, or leaving some branch vessel in the space un-occluded while using the space to anchor the embolization coil. This as a feature not encountered with Amplatz spiders or similar devices.

FIG. 6 shows the embolization coil 1 with an anchor deployed within an aneurysm 20 at the bifurcation of the common carotid artery 4 into the internal carotid artery 5 and external carotid 7 artery in the neck. This aneurysm is known as a bifurcation aneurysm. The embolization coil has transformed by virtue of its spring bias into the irregular shape shown, and fills a substantial portion of the aneurysm 20. The anchor 30 has also opened toward its unrestrained shape to the extent allowed by the aneurysm wall. The arms of the anchor are urged by spring force into contact with the aneurysm wall. The slight force applied by the spring bias of the anchor 30 on the wall anchors the embolization coil 1 into place, and prevents the coil from being washed out of the aneurysm by the high velocity blood flow at the bifurcation.

As can be seen by inspection of FIGS. 4 and 6, in a vessel with a diameter smaller than that of the unconstrained device, the device will be partially compressed. Consequently, the anchor will lean against the wall at multiple points resulting in a stable position. To achieve a good fixation the largest unconstrained diameter of the anchor is preferably equal to or slightly larger than twice the diameter of the vessel to be occluded. Sufficient anchoring power can be achieved with an anchor having an unrestrained diameter of the vessel, where the anchor is made of 0.010 inch stainless steel wires and the coil is anchored in high flow vessels. In moderate flow vessels, anchors made of 0.0075" stainless steel wire and having an unrestrained expanded diameter of slightly larger than the diameter of the target vessel provide adequate anchoring strength. The thickness, open diameter and length of the anchors may be varied to accommodate the numerous size blood vessels within the human body, as well as the fragility of the aneurysm or vessel wall.

Figure 7:
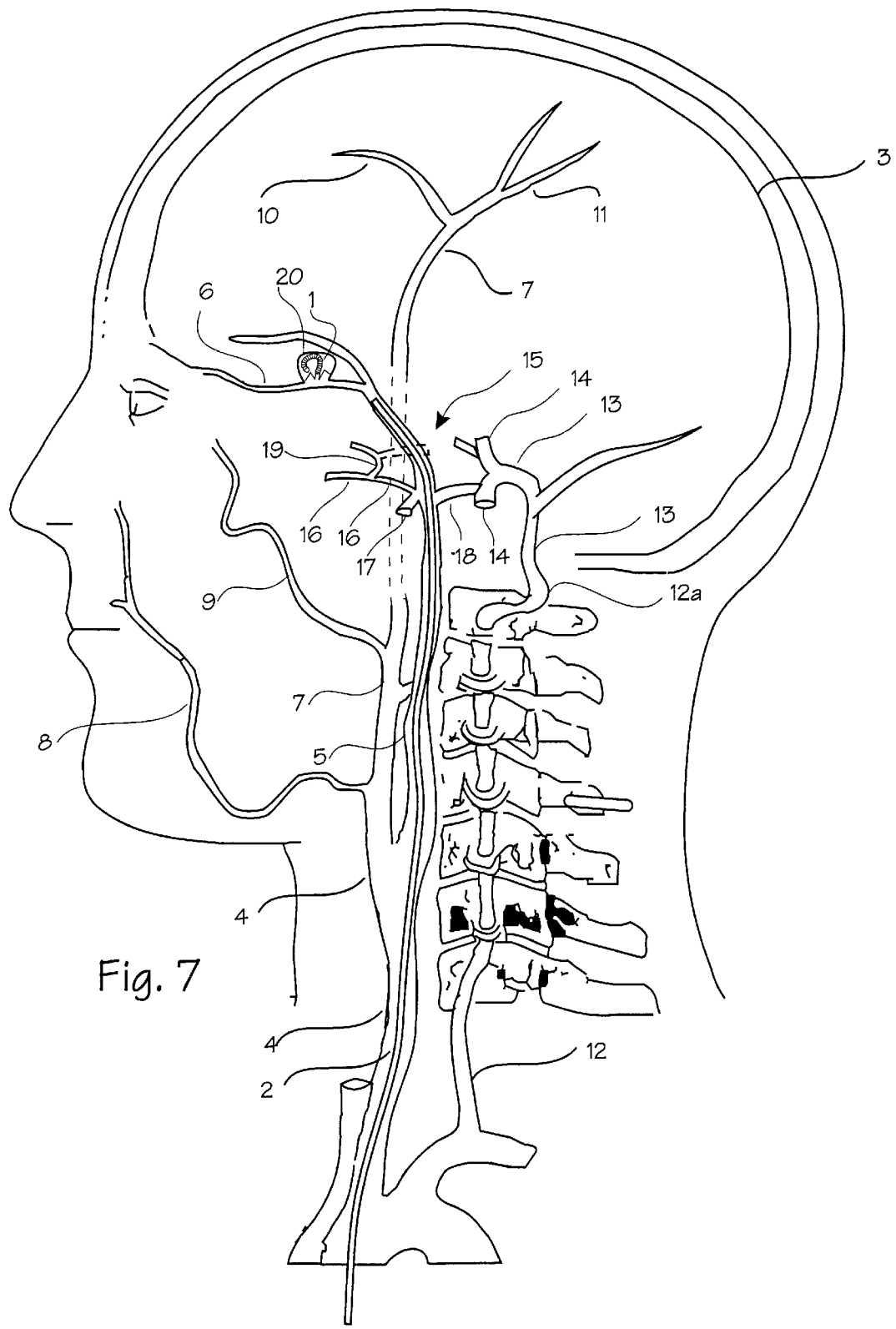
FIG. 7 is a schematic diagram of the vasculature of the brain showing a typical placement of a coil.

FIGS. 7 and 8 show the vasculature of the brain in sufficient detail to understand the invention. The brain 3 is supplied with blood through the carotid and the vertebral arteries on each side of the neck. The important arteries include the common carotid artery 4 in the neck, which will be the most common access pathway for the stent, the internal carotid 5 which supplies the opthalmic artery 6. The external carotid 7 supplies the maxillary artery 8, the middle meningeal artery 9, and the superficial temporal arteries 10

(frontal) and 11 (parietal). The vertebral artery 12 supplies the basilar artery 13 and the cerebral arteries including the posterior cerebral artery 14 and the circle of Willis indicated generally at 15. The siphon 12*a* of the vertebral artery appears in the intra-cranial vasculature on the vertebral approach to the Circle of Willis. Also supplied by the internal carotid artery are the anterior cerebral artery 16 and the middle cerebral artery 17, as well as the Circle of Willis, including the posterior communicating artery 18 and the anterior communicating artery 19. The siphon 5*a* of the internal carotid artery 5 appears in the intra-cranial vasculature on the carotid approach into the Circle of Willis. These arteries typically have an internal diameter of about 1 mm to 5 mm, most commonly from 2–4 mm. The methods and devices described herein allow access to these arteries and placement of occlusive coils in these arteries or into the aneurysms affecting these arteries. In FIG. 7, the insertion catheter 2 and occlusive coils 1 are shown threaded through the common carotid artery 4 and the internal carotid artery 5, with the coil extending into the aneurysm 20 illustrated in the opthalmic artery 6.

FIG. 8 shows the same blood vessels in a schematic view that better illustrates the Circle of Willis and the arteries which supply this important anatomic feature. The Circle of Willis 15 is a ring of arteries connecting the internal carotid arteries and the basilar artery (and hence the left and right vertebral arteries) to the anterior cerebral arteries 16, middle cerebral arteries 17 and posterior cerebral arteries 14. The system provides a redundant supply of blood to the cerebral arteries. The carotid siphon 5*a*, which forms an integral part of the internal carotid artery 5, is more clearly visible in this view. Aneurysms, fistulas, AVM's and tumors occurring inside the brain, in the intracranial portion of the carotid arteries, vertebral arteries (and the portions of those arteries distal to the siphons) and basilar artery, in the circle of Willis or even deeper within the brain may be treated with the occlusive coils and delivery systems described above. FIG. 8 shows an exemplary use in which a delivery catheter 2 is inserted through the aorta into the vertebral artery, the basilar artery, and into the Circle of Willis 15 to treat an aneurysm 20 which has occurred in this illustration at the bifurcation 21 where the basilar artery feeds into the right and left posterior cerebral arteries 14. The aneurysm is treated with occlusive coils 1 which are inserted into the aneurysm and delivered in place through the distal tip of the delivery catheter 2.

While the preferred embodiments of the devices and methods have been described in reference to the environment in which they were developed, they are merely illustrative of the principles of the inventions. It is expected that the devices will used to treat a variety of conditions within the intracranial vasculture in addition to those set forth above Other embodiments and configurations may be devised without departing from the spirit of the inventions and the scope of the appended claims.

We claim:

1. A method of treating vascular disease in an intracranial blood vessel comprising:

providing an anchored coil for occluding the intracranial vasculature at or near the site of vascular disease within the intracranial vasculature, said coil being provided with an anchor in the shape of an M or W, said coil being formed of wire and having an unrestrained expanded width exceeding the diameter of the intracranial blood vessel;

inserting the anchored coil into the intracranial blood vessel at or near the site of vascular disease and allowing the anchor to expand toward its unrestrained expanded width so as to come into engaging contact with the blood vessel and thereby anchor the coil in place within the intracranial blood vessel.

2. The method of claim 1, further comprising the step of inserting the anchored coil into the intracranial blood vessel through a percutaneous access pathway from a remote site in the vasculature of the body.

* * * * *